United States Patent [19]

Betlach, II

[11] Patent Number: 5,374,661
[45] Date of Patent: Dec. 20, 1994

[54] COMPOSITION AND METHOD FOR TRANSDERMAL DELIVERY OF DICLOFENAC

[75] Inventor: Charles J. Betlach, II, Pembroke Pines, Fla.

[73] Assignee: Sano Corporation, Pembroke Pines, Fla.

[21] Appl. No.: 32,724

[22] Filed: Mar. 16, 1993

Related U.S. Application Data

[63] Continuation of Ser. No. 725,352, Jul. 3, 1991, abandoned.

[51] Int. Cl.$^5$ ............................................. A01N 25/00
[52] U.S. Cl. ................................ 514/772.4; 514/944; 514/946; 514/887
[58] Field of Search .................. 424/449, 448, 78.05; 514/658, 944, 946, 772.4

[56] References Cited

U.S. PATENT DOCUMENTS

| | | | |
|---|---|---|---|
| 3,524,916 | 8/1970 | Mima et al. | 424/285 |
| 3,749,773 | 7/1973 | Ninger et al. | 514/180 |
| 4,009,254 | 2/1977 | Renold | 424/59 |
| 4,048,310 | 9/1977 | Chen et al. | 424/238 |
| 4,309,414 | 1/1982 | Inagi et al. | 514/420 |
| 4,341,783 | 7/1982 | Scheindlin | 424/253 |
| 4,407,824 | 10/1983 | Eckert | 514/555 |
| 4,424,234 | 1/1984 | Alderson et al. | 424/317 |
| 4,510,128 | 4/1985 | Khanna | 424/79 |
| 4,543,251 | 9/1985 | Kamishita | 424/81 |
| 4,545,992 | 10/1985 | Kamishita | 514/161 |
| 4,670,254 | 6/1987 | Kamishita | 424/81 |
| 4,687,781 | 8/1987 | Ehrenpreis et al. | 514/557 |
| 4,704,406 | 11/1987 | Stanislaus et al. | 514/570 |
| 4,710,497 | 12/1987 | Heller et al. | 514/221 |
| 4,711,906 | 12/1987 | von Stetten et al. | 514/561 |
| 4,738,848 | 4/1988 | Yoshida et al. | 424/448 |
| 4,778,786 | 10/1988 | Reever et al. | 514/54 |
| 4,789,667 | 12/1988 | Makino et al. | 514/161 |
| 4,851,426 | 7/1989 | Ladkani et al. | 514/420 |
| 4,859,696 | 8/1989 | Kamiya et al. | 514/240 |
| 4,873,081 | 10/1989 | Ogiso | 424/81 |
| 4,879,274 | 11/1989 | Kamiya et al. | 514/12 |
| 4,917,886 | 4/1990 | Asche | 424/81 |
| 4,946,870 | 8/1990 | Partain, III et al. | 514/777 |
| 4,948,581 | 8/1990 | Sawayanagi et al. | 424/81 |
| 4,948,588 | 8/1990 | Kamiya et al. | 424/436 |
| 4,952,560 | 8/1990 | Kigasawa et al. | 514/2 |
| 4,954,487 | 9/1990 | Cooper et al. | 514/159 |
| 4,996,193 | 2/1991 | Hewitt et al. | 514/11 |
| 4,999,379 | 3/1991 | Frankhauser | 514/567 |
| 5,095,037 | 3/1992 | Iwamitsu et al. | 514/561 |
| 5,164,416 | 11/1992 | Nagai et al. | 514/763 |

OTHER PUBLICATIONS

Kyuki et al., "Anti-Inflammatory Effect of Diclofenac–Sodium Ointment (Cream) in Topical Application", Japan J. Pharmacol., vol. 33, pp. 121–132 (1983).

Nishihata et al., "Percutaneous Absorption of Diclofenac in Rats and Humans: Aqueous Gel Formulation", Int. J. Pharm., vol. 46, pp. 1–7 (1988).

*Primary Examiner*—D. Gabrielle Phelan
*Attorney, Agent, or Firm*—Jones & Askew

[57] ABSTRACT

The topical drug delivery composition and method of the present invention provides a composition and method for delivering amounts of diclofenac effective for treating inflamed and/or painful joints or muscles percutaneously via a gel. Diclofenac sodium is solubilized in a mixture of water, a low molecular weight alcohol, and a glycol. In the present invention, the transdermal flux of diclofenac is unexpectedly enhanced by the addition of an ether alcohol and a fatty alcohol ester. The transdermal flux can be further enhanced by the addition of a glycol such as hexylene glycol.

4 Claims, 2 Drawing Sheets

COMPOSITION AND METHOD FOR TRANSDERMAL DELIVERY OF DICLOFENAC

This is a continuation of application Ser. No. 07/725,352 filed Jul. 3, 1991, now abandoned.

FIELD OF THE INVENTION

The present invention relates to a composition and method for topical delivery of an anti-inflammatory drug. More particularly, the present invention is a composition and method for increasing the transdermal permeation of diclofenac from a cosmetically acceptable gel preparation.

BACKGROUND OF THE INVENTION

Diclofenac sodium, sodium O-(2,6-dichlorophenyl)-acetate is a non-steroidal, anti-inflammatory drug. It is a phenylacetic acid derivative, which was designed based on known structure-activity relationships of other anti-inflammatory drugs. Diclofenac is a weak acid, pKa 4.0. It has a molecular weight of 318.1 and a partition coefficient into n-octanol from aqueous buffer, pH 7.4, of 13:4. Diclofenac can exist as many different salts of which diclofenac sodium is only one.

The chemical structure of diclofenac sodium is as follows:

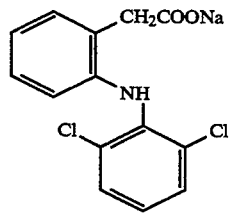

Diclofenac Sodium

Diclofenac demonstrates anti-inflammatory, antipyretic, and analgesic activity. It may be unique among non-steroidal, anti-inflammatory drugs in its pharmacological effect on the arachidonic acid cascade. Diclofenac inhibits the cyclooxygenase pathway with subsequent reduction in prostaglandin and thromboxane production. On a molar basis, diclofenac is 3 to 1000 times more potent than other nonsteroidal, anti-inflammatory drugs in inhibiting cyclooxygenase activity. Diclofenac also may inhibit the lipoxygenase pathway with subsequent reduction in leukotriene production. Leukotriene $B_4$ and other leukotrienes, to a lesser extent, are strong pro-inflammatory compounds. They promote chemotaxis, superoxide production, leukocyte aggregation, and lytic enzyme release. In addition, diclofenac reduces arachidonic acid availability by inhibiting its release and stimulating its reuptake.

The analgesic effect of diclofenac is due primarily to its peripheral action. This may result from diclofenac's inhibition of prostaglandin synthesis. Prostaglandins sensitize pain receptors to mechanical stimulation, and to other chemical mediators including, but not limited to, bradykinin and histamine. The anti-inflammatory effect of diclofenac also may contribute to the drug's analgesic effect. In addition. diclofenac's postulated effect on endorphin release from the pituitary may contribute to its analgesic effects.

Oral diclofenac therapy is associated with marked side effects. Adverse gastrointestinal reactions are the most frequent. The most common gastrointestinal side effects include nausea, vomiting, abdominal pain, dyspepsia and diarrhea. Less frequent side effects include abdominal distension, flatulence and peptic ulcers with bleeding. The incidence of adverse gastrointestinal reactions may approach 30 to 40 percent. These result both from local gastrointestinal irritation and from systemic inhibition of prostaglandin synthesis. Also, there may be an association between oral diclofenac use and hepatic toxicity (Please see Helfgott. S. M.; Snadberg-Cook, J.; Zakim, D. and Nestler, J. Diclofenac-Associated Hepatotoxicity. JAMA, 264; 2660–2662, 1990).

Topical application of diclofenac delivers the drug to the site of inflammation and minimizes diclofenac levels in the gastrointestinal and circulatory systems. Undesirable side effects resulting from oral administration of the drug are greatly reduced and, properly administered in the manner disclosed herein, the topical application produces therapeutic benefits.

Examples of such a topical preparation are found in U.S. Pat. No. 4,543,251 and U.S. Pat. No. 4,670,254 to Kamishita which disclose diclofenac stabilized in a medium comprising water, a lower alkanol, a glycol and a neutralizing agent to which a gelling agent is added. It should be noted that Kamishita does not teach or suggest the use of flux enhancers, moisturizers, or emollients in his gel formulation.

However, the effectiveness of topical diclofenac in treating inflammation and/or painful joints and muscles depends significantly on the particular skin penetrating vehicle with which it is used. To attain effective diclofenac concentrations in a joint's synovial fluid or in a muscle, the gel must have a high transdermal permeation. What is needed is a composition and method for optimizing the transdermal flux of the externally applied diclofenac in order to increase the likelihood of its therapeutic effectiveness.

In addition the vehicle in which topical diclofenac is delivered must by cosmetically acceptable. Because the drug is applied externally, it must be administered periodically due to washing or wearing off. Repeated exposure to alcohol and/or glycol containing gel preparations results in irritation or drying of the skin. Because this is not pleasant, patients tend to stop using the drug, or do not use it according to the proper schedule. When the drug is not applied in the optimal manner, because of the unpleasant delivery system, the condition for which the drug is applied is not optimally treated. What is needed is a topical delivery system that can comfortably used and that will encourage consistent and continuous application needed to achieve optimal and reliable effectiveness.

SUMMARY OF THE INVENTION

The topical drug delivery composition and method of the present invention provides a composition and method for delivering amounts of diclofenac effective for treating inflamed and/or painful joints or muscles percutaneously via a gel. Diclofenac is solubilized in a mixture of water, a low molecular weight alcohol, and a glycol. In the present invention, the transdermal flux of diclofenac is unexpectedly enhanced by the addition of ether alcohols and fatty alcohols ester. The transdermal flux can be further enhanced by the addition of glycols such as hexylene glycol.

In the present invention, the consistent and continuous application needed to achieve optimal and reliable effectiveness of the diclofenac is encouraged by the addition of a skin moisturizer and an emollient.

Accordingly, it is an object of the present invention to deliver by topical application a therapeutically effective amount of diclofenac over a period of time to a local site.

It is another object of the present invention to deliver by topical application a therapeutic amount of diclofenac over a period of time to an arthritic joint.

It is another object of the present invention to deliver by topical application a therapeutic amount of diclofenac over a period of time to the synovial fluid of an inflamed or painful joint.

It is another object of the present invention to deliver by topical application a therapeutic amount of diclofenac over a period of time to an inflamed or painful muscle.

It is yet another object of the present invention to provide a method of treating local inflammation and pain of joints or muscles without the use of oral diclofenac.

It is another object of the present invention to reduce the gastrointestinal side-effects of oral diclofenac.

It is another object of the present invention to reduce the systemic side-effects of oral diclofenac.

It is another object of the present invention to increase the transdermal flux of diclofenac over a basic gel formulation which contains water, ethanol, propylene glycol, triethanolamine, and a carboxyvinyl polymer.

It is another object of the present invention to increase the transdermal flux of diclofenac by the use of a mixture of a fatty alcohol ester and an ether alcohol.

It is another object of the present invention to increase the transdermal flux of diclofenac by the use of ether alcohols and fatty alcohols ester.

It is another object of the present invention to provide a cosmetically elegant diclofenac gel preparation.

It is another object of the present invention to deliver diclofenac to a local site while maintaining the cosmetic stability of the skin at the site of application.

It is another object of the present invention to avoid skin drying and to maintain the integrity of the skin during chronic use.

It is another object of the present invention to provide a topical drug delivery composition and method which softens and soothes the skin.

It is another object of the present invention to provide a topical drug delivery composition and method which reduces clinical problems often associated with topical delivery vehicles, such as dry, cracked, red, irritated skin.

It is another object of the present invention to provide a topical drug delivery composition and method which is aesthetically pleasing.

It is another object of the present invention to increase the chronic wearability of the gel preparation.

These and other objects, features and advantages of the present invention will become apparent after a review of the following detailed description of the disclosed embodiments and the appended claims.

DETAILED DESCRIPTION

Figure 1:
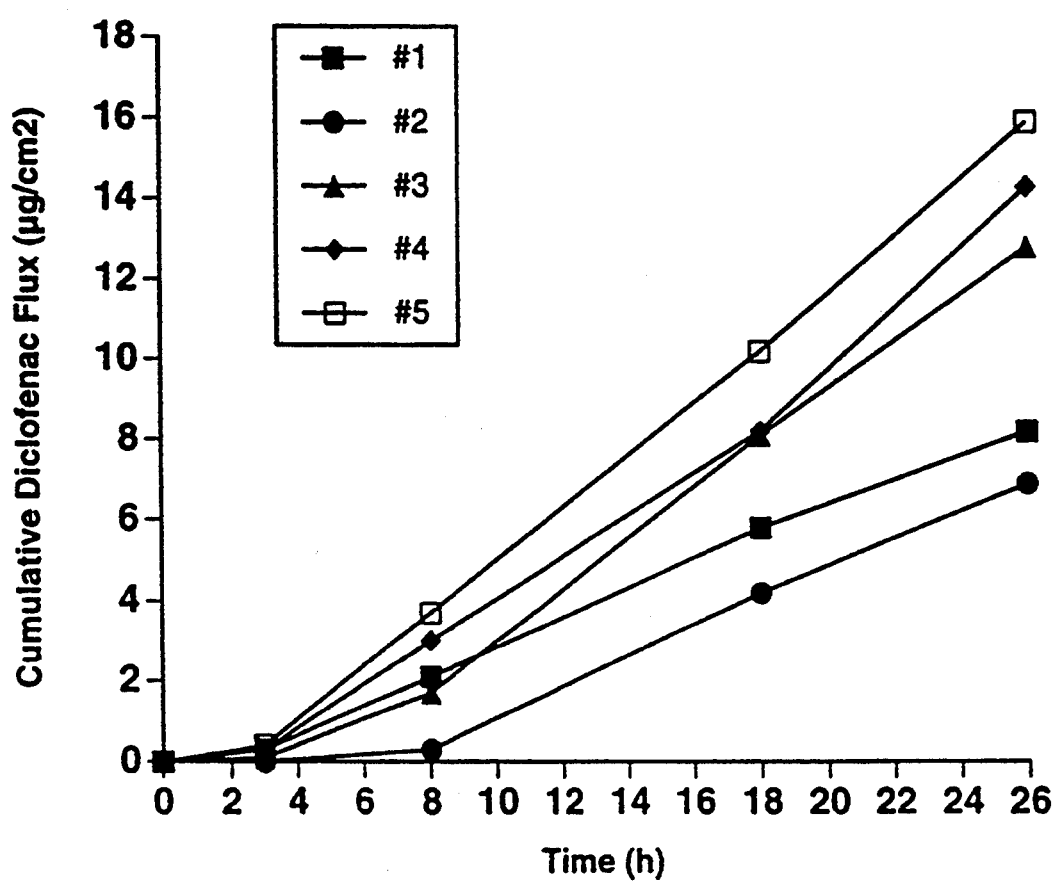
FIG. 1 compares the transdermal permeation of diclofenac from the gel preparations described in Example 1 through Example 5 across human cadaver skin. The cumulative amount of diclofenac crossing the skin is plotted as a function of time.

The present invention relates to an improved anti-inflammatory composition and method. The composition contains a therapeutically effective amount of diclofenac. A therapeutically effective amount of diclofenac is defined herein as an amount of diclofenac effective for treating inflamed and/or painful joints or muscles. The composition according to the present invention also includes a medium capable of dissolving the diclofenac salt. This medium contains lower molecular weight alcohols, glycols, ether alcohols and fatty alcohols ester. In addition, the composition contains neutralizing agents and thickening agents.

It is to be understood the active ingredient is the diclofenac compound and the present invention encompasses all of the salts of diclofenac. The preferred salt is diclofenac sodium. The concentration range of diclofenac in the present invention is between approximately 0.1% to 2.5% with a preferred concentration of approximately 1%.

It has been discovered that the addition of a glycol containing between approximately two and eight carbon atoms enhances the transdermal delivery of diclofenac. The preferred glycols include, but are not limited to, propylene glycol, butylene glycol, dipropylene glycol, diethylene glycol, triethylene glycol, the most preferred glycol being hexylene glycol. The concentration range of hexylene glycol in the present invention is between approximately 0.5% and 20% with a preferred concentration of approximately 10%.

Optionally the anti-inflammatory composition of the present invention contains moisturizers effective for hydrating the skin and emollients effective for softening and smoothing the skin. Moisterizers and emollients which can be used in the present invention are well known to those of ordinary skill in the art.

The low molecular weight alcohols which can be used in this invention include, but are not limited to, ethanol, isopropyl alcohol, propyl alcohol, n-butyl alcohol, hexyl alcohol and benzyl alcohol. The amount of low molecular weight alcohol used is high enough to solubilize the diclofenac but is low enough to minimize the drying effect of chronic alcohol use on the skin. The low molecular weight alcohols can be used singly or in combination in an amount ranging from approximately 1% to 50% [weight/weight]. The more preferred concentration is in the range of approximately 10% to 20%.

The thickening agents used in the present invention include, but are not limited to, carboxyvinyl polymers and aloe vera gel. The carboxyvinyl polymers are used as gelating agents. Suitable commercially available carboxyvinyl polymers include, but are not limited to, Carbomer 934P or Carbomer 940 (B.F. Goodrich Company, Cleveland, Ohio). The carboxyvinyl polymers are used in an amount ranging from approximately 0.5% to 3.0% with a preferred amount ranging from approximately 1.2% to 2.0%. A thickening agent such as, but not limited to, aloe vera gel (Terry Laboratories, Inc., Melbourne, Fla.) can be used in addition to the carboxyvinyl polymer. The aloe vera gel is used in an amount ranging from approximately 0.005% to 2.0%. Aloe vera gel has moisturizing properties which help to insure proper hydration of the skin.

Ether alcohols and fatty alcohols ester are included to enhance the transdermal permeation of diclofenac. The preferred ether alcohols include, but are not limited to, butoxydiglycol, ethoxyethanol, methoxyethanol, phenoxydiglycol, phenoxyethanol, phenoxyisopropanol, methoxypropanol and methoxydiglycol, the most preferred being ethoxydiglycol. The preferred fatty alcohols ester range between approximately C9 to C15 with the most preferred fatty alcohols ester being C12 to C15 alcohols benzoate and C12 to 15 alcohols lactate and C12 to C15 alcohols octanoate. The ratio of diglycol:fatty alcohol ester can range from approximately 0.5:0.1 to 5:4, the most preferred ratio being approximately 2.5:1.2. The fatty alcohols ester also soften and smooth the skin and impart a dry, non-greasy lubricating feel to the skin thereby increasing patient acceptance.

The transdermal permeation of diclofenac is further enhanced by inclusion of glycols containing 2 to 8 carbons such as, but not limited to, glycol, dipropylene glycol, triethylene glycol and hexylene glycol. These glycols can be used in addition to or in place of, the ethylene glycol, propylene glycol, or butylene glycol known to solubilize and stabilize diclofenac. The glycols can be used singly or in combination. The total amount of glycols included in the anti-inflammatory gel preparation of the present invention may range from approximately 0.5% to 20%, more advantageously from 5% to 15%, and most advantageously at approximately 10%.

The agent capable of neutralizing the composition can include a wide variety of compounds or combinations of compounds including, but not limited to, aliphatic amines such as diethanolamine, ethanolamine, isopropanolamine, isopropylamine and tetrahydroxypropyl ethylenediamine. By neutralizing the composition, the pH is adjusted to between approximately 5.5 to 7.5. The preferred agent for neutralizing the composition is triethanolamine. Enough of the triethanolamine is added to bring the pH to the desired range.

The present invention also includes a method of treating inflamed and/or painful joints or muscles comprising the step of administering to the skin a composition containing a therapeutically effective amount of diclofenac. A therapeutically effective amount of diclofenac is defined herein as an amount of diclofenac that is effective for treating inflamed and/or painful joints or muscles. A thickening agent is added to the composition which is contemplated as the present invention. The composition according to the present invention also includes a medium which is capable of dissolving the diclofenac salt. This medium contains lower molecular weight alcohols, glycols, ether alcohols and fatty alcohols ester. In addition, the composition contains an agent capable of neutralizing the composition. The composition is preferably administered two to three times per day. The daily topical dose ranges between approximately 5 mg to 150 mg of diclofenac sodium.

This invention is further illustrated by the following examples, which are not to be construed in any way as imposing limitations upon the scope thereof. On the contrary, it is to be clearly understood that resort may be had to various other embodiments, modifications, and equivalents thereof which, after reading the description herein, may suggest themselves to those skilled in the art without departing from the spirit of the present invention and/or the scope of the appended claims.

EXAMPLE 1

This basic gel is composed of a gelling or thickening agent comprising a carboxyvinyl polymer such as Carbomer 934P, ethanol, propylene glycol, triethanolamine and water (U.S. Pat. No. 4,543,251 and U.S. Pat. No. 4,670,254 to Kamishita) (Table I). Ethanol, propylene glycol and water serve as the liquid in the gel and are required to dissolve the diclofenac. Triethanolamine is a standard neutralizing agent.

A cocktail is prepared containing diclofenac (1.0 g), ethanol (17.1 g) and propylene glycol (10 g). A 5% Carbomer 934P gel is prepared with purified water and Carbomer 934P powder. Ten grams of water are added with stirring to 40 g of the 5% Carbomer gel. To this is added the cocktail with mixing. Triethanolamine (1.3 g) is added to bring the pH to approximately 6.0. The remainder of the purified water is added to bring the total weight to 100 g.

TABLE I

| Basic Diclofenac Gel | |
|---|---|
| Ingredient | Amount (g) |
| Diclofenac Sodium | 1.0 |
| Carbomer 934P | 2.0 |
| Triethanolamine | 1.3 |
| Ethanol | 17.1 |
| Propylene Glycol | 10.0 |
| Water | 68.6 |

EXAMPLE 2

A cocktail is prepared containing diclofenac sodium (1.0 g), ethanol (17.1 g), ethoxydiglycol (2.5 g) and propylene glycol (10 g). A 5% Carbomer 934P gel is prepared with purified water and Carbomer 934P powder. Ten grams of water is added with stirring to 40 g of the 5% Carbomer gel. To this is added the cocktail with mixing. Triethanolamine (1.3 g) is added to bring the pH to approximately 6.0. The remainder of the purified water is added to bring the total weight to 100 g.

EXAMPLE 3

A cocktail is prepared containing diclofenac sodium (1.0 g), ethanol (17.1 g), C12–15 alcohols benzoate (1.2 g), and propylene glycol (10 g). A 5% Carbomer 934P gel is prepared with purified water and Carbomer 934P powder. Ten grams of water is added with stirring to 40 g of the 5% Carbomer gel. To this is added the cocktail with mixing. Triethanolamine (1.3 g) is added to bring the pH to approximately 6.0. The remainder of the purified water is added to bring the total weight to 100 g.

EXAMPLE 4

A gel is prepared in the same manner as Examples 1 and 2, and it contains the ingredients listed in Table II:

TABLE II

| Ingredient | Amount (g) |
|---|---|
| Diclofenac Sodium | 1.0 |
| Carbomer 934P | 2.0 |
| Triethanolamine | 1.3 |
| Ethanol | 17.1 |
| Propylene Glycol | 10.0 |

TABLE II-continued

| Ingredient | Amount (g) |
| --- | --- |
| Ethoxydiglycol | 2.5 |
| C12-15 alcohols benzoate | 1.2 |
| Purified Water | 64.9 |

EXAMPLE 5

A cocktail is prepared containing diclofenac sodium (1.0 g), ethanol (17.1 g), C12-15 alcohols benzoate (1.2 g), ethoxydiglycol (2.5 g), and propylene glycol (10 g). A 5% Carbomer 934P gel is prepared with purified water and Carbomer 934P powder. Ten grams of purified water containing aloe vera gel (0.5 g) is added with stirring to 40 g of the 5% Carbomer gel. To this is added the cocktail with mixing. Triethanolamine (1.3 g) is added to bring the pH to approximately 6.0. The remainder of the purified water is added to bring the total weight to 100 g.

EXAMPLE 6

A cocktail is prepared containing diclofenac sodium (1.0 g), ethanol (17.1 g), C12-15 alcohols benzoate (0.6 g), ethoxydiglycol (2.5 g) and propylene glycol (10 g). A 5% Carbomer 934P gel is prepared with purified water and Carbomer 934P powder. Ten grams of water is added with stirring to 40 g of the 5% Carbomer gel. To this is added the cocktail with mixing. Triethanolamine (1.3 g) is added to bring the pH to approximately 6.0. The remainder of the purified water is added to bring the total weight to 100 g.

EXAMPLE 7

A cocktail is prepared containing diclofenac sodium (1.0 g), ethanol (17.1 g), C12-15 alcohols benzoate (0.6 g), ethoxydiglycol (5.0 g) and propylene glycol (10 g). A 5% Carbomer 934P gel is prepared with purified water and Carbomer 934P powder. Ten grams of water is added with stirring to 40 g of the 5% Carbomer gel. To this is added the cocktail with mixing. Triethanolamine (1.3 g) is added to bring the pH to approximately 6.0. The remainder of the purified water is added to bring the total weight to 100 g.

EXAMPLE 8

A cocktail is prepared containing diclofenac sodium (1.0 g), ethanol (17.1 g), C12-15 alcohols benzoate (2.5 g), ethoxydiglycol (2.5 g) and propylene glycol (10 g). A 5% Carbomer 934P gel is prepared with purified water and Carbomer 934P powder. Ten grams of water is added with stirring to 40 g of the 5% Carbomer gel. To this is added the cocktail with mixing. Triethanolamine (1.3 g) is added to bring the pH to approximately 6.0. The remainder of the purified water is added to bring the total weight to 100 g.

EXAMPLE 9

A cocktail is prepared containing diclofenac sodium (1.0 g), ethanol (17.1 g), C12-15 alcohols benzoate (1.2 g), ethoxydiglycol (2.5 g), and dipropylene glycol (10 g). A 5% Carbomer 934P gel is prepared with purified water and Carbomer 934P powder. Ten grams of purified water containing aloe vera gel (0.5 g) is added with stirring to 40 g of the 5% Carbomer gel. To this is added the cocktail with mixing. Triethanolamine (1.3 g) is added to bring the pH to approximately 6.0. The remainder of the purified water is added to bring the total weight to 100 g.

EXAMPLE 10

A cocktail is prepared containing diclofenac sodium (1.0 g), ethanol (17.1 g), C12-15 alcohols benzoate (1.2 g), ethoxydiglycol (2.5 g), and hexylene glycol (10 g). A 5% Carbomer 934P gel is prepared with purified water and Carbomer 934P powder. Ten grams of purified water containing aloe vera gel (0.5 g) is added with stirring to 40 g of the 5% Carbomer gel. To this is added the cocktail with mixing. Triethanolamine (1.3 g) is added to bring the pH to approximately 6.0. The remainder of the purified water is added to bring the total weight to 100 g.

EXAMPLE 11

Human Skin Flux Tests

Flux of diclofenac through human cadaver skin is studied using modified Franz Diffusion Cells (Crown Glass Company, Inc., Somerville, N.J.). Samples of whole skin are removed from the abdomen of a human cadaver not later than 48 hours postmortem. The skin is stored frozen ($-20°$ C.) until ready for use. The frozen skin is thawed as needed and the epidermis is isolated from the skin by immersing the skin in water at 60° C. for 30 seconds. This epidermis is used in the skin flux studies. The flux is performed at 37° C. and the samples are collected into normal saline. Serial samples are taken over a 26 hour period.

The flux rates of diclofenac from Examples 1 to 5 are presented in Table III. Flux rates at 5.5 hours (3 to 8 h interval) are presented here. The cumulative skin flux of these Examples (1 through 5) are illustrated in FIG. 1. The addition of ethoxydiglycol alone (Example 2) to the basic gel (Example 1) decreases the diclofenac flux. The addition of C12-15 alcohols benzoate alone (Example 3) to the basic gel provides little flux change before 8 hours, after which time the flux increased. However, the addition of ethoxydiglycol along with C12-15 alcohols benzoate causes a significant increase in the flux during the early hours as well as later.

TABLE III

The effect of ethoxydiglycol and C12-15 alcohols benzoate on the human skin flux of diclofenac.

| Ingredient | Amount (%) | | | | |
| --- | --- | --- | --- | --- | --- |
| | Ex. 1 | Ex. 2 | Ex. 3 | Ex. 4 | Ex. 5 |
| Diclofenac Sodium | 1.0 | 1.0 | 1.0 | 1.0 | 1.0 |
| Carbomer 934P | 2.0 | 2.0 | 2.0 | 2.0 | 2.0 |
| Triethanolamine | 1.3 | 1.3 | 1.3 | 1.3 | 1.3 |
| Ethanol | 17.1 | 17.1 | 17.1 | 17.1 | 17.1 |
| Propylene Glycol | 10.0 | 10.0 | 10.0 | 10.0 | 10.0 |
| Ethoxydiglycol | 0 | 2.5 | 0 | 2.5 | 2.5 |
| C12-15 alcohols benzoate | 0 | 0 | 1.2 | 1.2 | 1.2 |
| Aloe vera gel | 0 | 0 | 0 | 0 | 0.5 |
| Purified Water | 68.6 | 66.1 | 67.4 | 64.9 | 64.4 |
| Mean Skin Flux ($\mu g/cm^2/h$) | 0.368 | 0.116 | 0.288 | 0.508 | 0.595 |
| Cosmetic Appeal | 2 | 2 | 3 | 3 | 4 |

Figure 2:
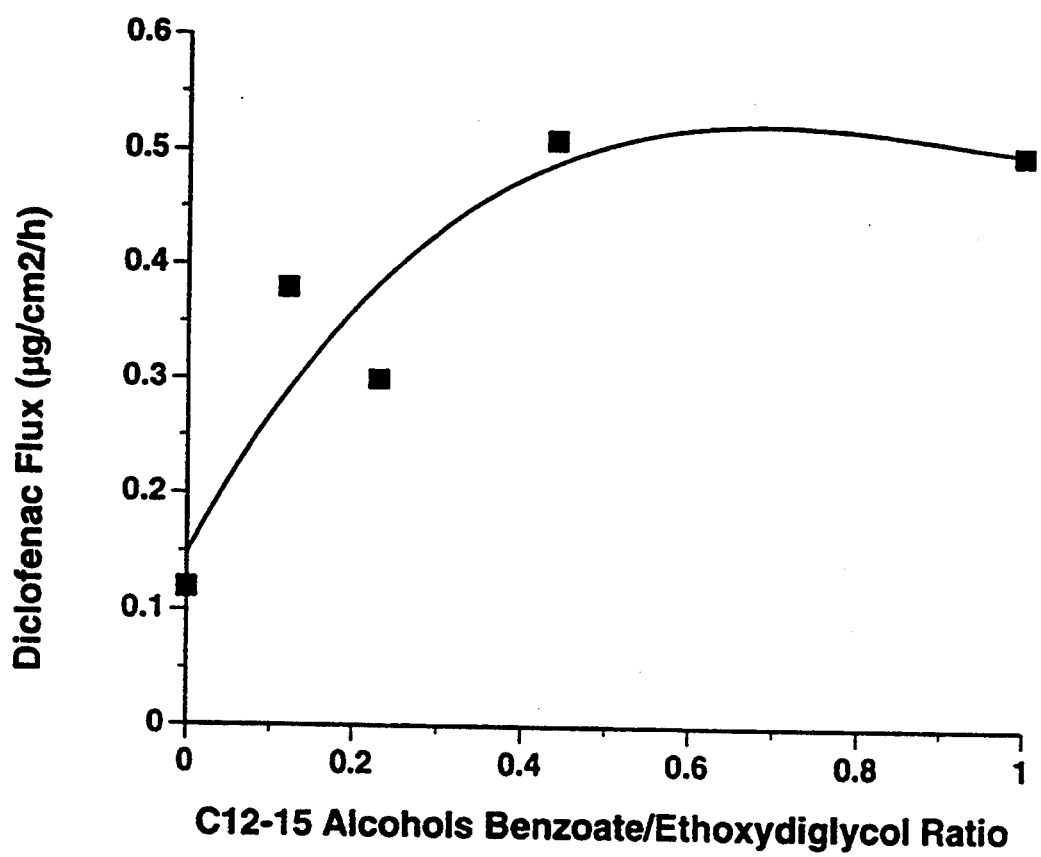
FIG. 2 shows the effect of different ratios of ethoxydiglycol and C12-15 alcohols benzoate on the transdermal permeation of diclofenac across human cadaver skin.

The ratio of C12-15 alcohols benzoate/ethoxydiglycol is refined by examining the skin flux in formulas with various ratios (Examples 2, 4, 6, 7 and 8). The results (FIG. 2) illustrate that the flux increases with increasing ratio to a plateau. The ratio of 1.2:2.5, C12-15 alcohols benzoate:ethoxydiglycol, is at the top of the incline and provides the maximum skin flux.

The cosmetic appeal of each product was rated such that a rating of 5 is the best cosmetic appeal and 0 is the worse. The addition of aloe vera gel increases the diclofenac skin flux slightly (Table III and FIG. 1). Example 5 (containing the ethoxydiglycol, C12–15 alcohols benzoate and aloe vera gel have the highest flux for Examples 1 through 5.

Examples 5, 9 and 10 look at the effect of different glycols on flux rate. Glycols that are compared are propylene glycol, dipropylene glycol and hexylene glycol. Table IV lists the flux through human skin with these glycols:

TABLE IV

The effect of different glycols on the human skin flux of diclofenac.

| Example | Glycol | Mean Skin Flux ($\mu g/cm^2/h$) |
|---|---|---|
| 5 | Propylene Glycol | 0.595 |
| 9 | Dipropylene Glycol | 0.786 |
| 10 | Hexylene Glycol | 0.879 |

As can be seen from this data, the skin flux increases with dipropylene glycol and hexylene glycol.

While the invention has been described in detail and with reference to specific embodiment thereof, it will be apparent to one skilled in the art that various changes and modifications can be made therein without departing from the spirit and scope thereof.

I claim:

1. A composition comprising:
   a. a therapeutically effective amount of diclofenac sodium;
   b. a thickening agent;
   c. a medium containing:
      i. approximately 1% to 50% of a lower molecular weight alcohol;
      ii. approximately 0.5% to 20% of a glycol;
      iii. an ether alcohol and a fatty alcohol ester; and
      iv. water; and
   d. an agent capable of neutralizing the composition; wherein the lower molecular weight alcohol is a C-2 to a C-6 alcohol, wherein the ether alcohol is ethoxydiglycol and the fatty alcohol ester is selected from the group consisting of C12 to C15 alcohols benzoate, where the ratio of ethoxydiglycol to fatty alcohol ester is within the range of approximately 0.5 to 5 ethoxydiglycol: 0.1 to 4 fatty alcohol ester.

2. The composition of claim 1, wherein the ratio of ethoxydiglycol to fatty alcohol ester is approximately 2.5 ethoxydiglycol:1.2 fatty alcohol ester.

3. A method for treating a patient with inflamed and painful joints comprising the step of administering to the skin of the patient a composition comprising:
   a. a therapeutically effective amount of diclofenac sodium;
   b. a thickening agent;
   c. a medium containing:
      i. approximately 1% to 50% of a lower molecular weight alcohol;
      ii. approximately 0.5% to 20% of a glycol;
      iii. an ether alcohol and a fatty alcohol ester; and
      iv. water; and
   d. an agent capable of neutralizing the composition; wherein the ether alcohol is ethoxydiglycol and the fatty alcohol ester is selected from the group consisting of C12 to C15 alcohols benzoate, and where the ratio of ethoxydiglycol to fatty alcohol ester is within the range of approximately 0.5 to 5 ethoxydiglycol: 0.1 to 4 fatty alcohol ester.

4. The method of claim 3, wherein the ratio of ethoxydiglycol to fatty alcohol ester is approximately 2.5 ethoxydiglycol:1.2 fatty alcohol ester.

* * * * *